(12) United States Patent
Qin et al.

(10) Patent No.: US 10,538,481 B2
(45) Date of Patent: Jan. 21, 2020

(54) METHOD FOR PURIFYING 1,5-PENTANEDIAMINE AND 1,5-PENTANEDIAMINE

(71) Applicants: Cathay Biotech Inc., Shanghai (CN); CIBT America Inc., Newark, DE (US)

(72) Inventors: Bingbing Qin, Shanghai (CN); Charlie Liu, Shanghai (CN); Shanshi Guo, Shanghai (CN); Benliang Hou, Shanghai (CN); Xiucai Liu, Shanghai (CN)

(73) Assignees: Cathay Biotech Inc., Shanghai (CN); CIBT America Inc., Newark, DE (US)

( * ) Notice: Subject to any disclaimer, the term of this patent is extended or adjusted under 35 U.S.C. 154(b) by 27 days.

(21) Appl. No.: 15/537,168

(22) PCT Filed: Dec. 17, 2014

(86) PCT No.: PCT/CN2014/094124
§ 371 (c)(1),
(2) Date: Jun. 16, 2017

(87) PCT Pub. No.: WO2016/095136
PCT Pub. Date: Jun. 23, 2016

(65) Prior Publication Data
US 2018/0002272 A1    Jan. 4, 2018

(51) Int. Cl.
C07C 211/09 (2006.01)
C07C 209/84 (2006.01)
C07C 209/00 (2006.01)
C07C 209/82 (2006.01)

(52) U.S. Cl.
CPC .......... C07C 211/09 (2013.01); C07C 209/00 (2013.01); C07C 209/82 (2013.01); C07C 209/84 (2013.01)

(58) Field of Classification Search
None
See application file for complete search history.

(56) References Cited

U.S. PATENT DOCUMENTS

| | | | |
|---|---|---|---|
| 3,510,522 A | 5/1970 | Cureton et al. | |
| 2008/0076049 A1* | 3/2008 | Saban | C07C 227/16 430/58.05 |

FOREIGN PATENT DOCUMENTS

| | | |
|---|---|---|
| CN | 1609107 A | 4/2005 |
| CN | 1829680 A | 9/2006 |
| CN | 102449029 A | 5/2012 |
| CN | 103347852 A | 10/2013 |
| CN | 104098508 A | 10/2014 |
| EP | 0262562 * | 4/1988 |
| EP | 2415801 A1 | 2/2012 |
| EP | 2684867 A1 | 1/2014 |
| JP | S4852708 A | 7/1973 |
| JP | H04312556 A | 11/1992 |
| JP | H0565261 A | 3/1993 |
| JP | H06025410 A | 2/1994 |
| JP | 2003292614 A | 10/2003 |
| JP | 2007516159 A | 6/2007 |
| JP | 2011201863 A | 10/2011 |
| WO | 2005000785 A1 | 1/2005 |
| WO | 2010113736 A1 | 10/2010 |
| WO | 2012121291 A1 | 9/2012 |
| WO | 2015076238 A1 | 5/2015 |

OTHER PUBLICATIONS

European Search Report for EP14908171.3 dated Aug. 8, 2018.

* cited by examiner

*Primary Examiner* — Sudhakar Katakam
*Assistant Examiner* — Jennifer C Sawyer
(74) *Attorney, Agent, or Firm* — Fox Rothschild LLP

(57) ABSTRACT

Provided is a method for purifying 1,5-pentanediamine comprising: providing 1,5-pentanediamine to be purified and treating the 1,5-pentanediamine to be purified by a reduction reaction to obtain purified 1,5-pentanediamine. Meanwhile, further provided is 1,5-pentanediamine prepared by the method. The purification method has a concise process and a simple operation, and is suitable for industrial production, and can significantly improve the quality of 1,5-pentanediamine.

5 Claims, No Drawings

METHOD FOR PURIFYING 1,5-PENTANEDIAMINE AND 1,5-PENTANEDIAMINE

TECHNICAL FIELD

The present invention relates to a method for purifying 1,5-pentanediamine, and 1,5-pentanediamine obtained by the method.

BACKGROUND

Pentanediamine (pentanediamine mentioned in the present invention refers to 1,5-pentanediamine, alias 1,5-diaminopentane, pentamethylene diamine, cadaverine) is an important chemical intermediate, mainly used as a monomer for preparing polymers such as polyamides, an organic synthesis intermediate, and an epoxy resin curing agent, and also used for biological research. Nylons, which are obtained by polymerization of 1,5-pentanediamine, can be used in many aspects of daily production and life, such as electronic appliances, mechanical equipment, and automobile parts.

Industrially, the process for preparing 1,5-pentanediamine is as follows: a solution of 1,5-pentanediamine salt is obtained by fermentation or enzymatic conversion process; the salt solution is treated by adding alkali, extraction and evaporation and the like to obtain an aqueous solution of 1,5-pentanediamine, followed by distillation to give 1,5-pentanediamine. In the preparation of 1,5-pentanediamine, in addition to 1,5-pentanediamine, by-products containing an unsaturated bond, such as 2,3,4,5-tetrahydropyridine (THP), are also produced.

In the process for preparing nylons with 1,5-pentanediamine as the starting material, the presence of the unsaturated by-product THP would affect the subsequent polymerization of 1,5-pentanediamine, thereby reducing the product quality of the polymer such as nylon 56. In particular, THP would cause the discoloration or branching of the polymer. Thus, reducing the amount of impurity THP in the 1,5-pentanediamine product can avoid the discoloration of the polymer and is critical to the improvement of the quality of the polymer product.

In the prior art relating to the removal and effective control of impurity THP, as described in EP 26684867 of Mitsui Chemicals, the fatty alcohols having 4 to 7 of carbon atoms are used as extractant to extract 1,5-pentanediamine from a fermentation broth, which can effectively reduce the THP content in the 1,5-pentanediamine products. Taking n-butanol as an example, the extraction rate thereof is 91.6%, the content of THP in the product is 0.1 wt %; and when using isobutanol as solvent, the extraction rate is 86.0%, the content of the impurity THP in the product is 0.1 wt %, and when using chloroform as extractant, the extraction rate is only 61.7%, the content of the impurity THP in the product is 0.6 wt %. Although the extraction by fatty alcohol with 4 to 7 of carbon atoms may obtain a better result than using chloroform as extractant, such extraction still has some defects such as relatively low extraction rate, difficulty in the separation of the layers, and high energy consumption in recovery of the extractant, and is not suitable for large-scale production.

As described in CN102449029 of TORAY INDUSTRIES, INC., the polyamide resins obtained by polymerizing 1,5-pentanediamine having a total content of 0.1% of THP and piperidine have better performance and quality, wherein the extraction process of the amine raw material is carried out by using chloroform as extractant and further distillation under reduced pressure to obtain 1,5-pentanediamine with the total content of impurities THP and piperidine less than 0.1%. Clearly, the extraction rate of chloroform is relatively low, as a result, a large amount of 1,5-pentanediamine present in the aqueous phase is not effectively extracted, thus the product yield is low, and the loss is significant.

Therefore, how to remove and effectively control the content of impurity THP in 1,5-pentanediamine products has become a key factor in controlling the quality of 1,5-pentanediamine products and a "bottle neck" for improving the quality of nylon products prepared by 1,5-pentanediamine.

SUMMARY OF THE INVENTION

In order to solve the technical problems mentioned above, the present invention provides a method for purifying 1,5-pentanediamine, comprising: providing 1,5-pentanediamine to be purified; and treating said 1,5-pentanediamine to be purified by use of reduction reaction, to obtain a purified 1,5-pentanediamine.

According to an embodiment of the present invention, the 1,5-pentanediamine to be purified contains 2,3,4,5-tetrahydropyridine impurity.

According to another embodiment of the present invention, the content of 2,3,4,5-tetrahydropyridine impurity in the purified 1,5-pentanediamine is less than 0.05 wt %.

According to another embodiment of the present invention, the content of the 2,3,4,5-tetrahydropyridine impurity in the purified 1,5-pentanediamine is less than 0.03 wt %.

According to another embodiment of the present invention, the purified 1,5-pentanediamine contains piperidine.

According to another embodiment of the present invention, the purification further comprises a distillation step to remove piperidine formed by the reduction of 2,3,4,5-tetrahydropyridine, so as to keep the content of piperidine in the purified 1,5-pentanediamine less than 0.05 wt %, based on the weight of 1,5-pentanediamine in the 1,5-pentanediamine to be purified.

According to another embodiment of the present invention, the content of piperidine in the purified 1,5-pentanediamine is less than 0.03 wt %.

According to another embodiment of the present invention, the reduction reaction is an electrochemical reduction or a reduction with reducing agent, and the reducing agent is hydrogen gas or metal hydride.

According to another embodiment of the present invention, the metal hydride is one or more selected from the group consisting of $NaBH_4$, $KBH_4$, and $LiAlH_4$.

According to another embodiment of the present invention, when the metal hydride is used as the reducing agent, the reaction temperature is from 0 to 25° C., the reaction time is from 0.5 to 1 hour, and the metal hydride is from 1 to 2 times of 2,3,4,5-tetrahydropyridine in the 1,5-pentanediamine to be purified in the amount of substance.

According to another embodiment of the present invention, when hydrogen gas is used as the reducing agent, a nickel-based catalyst or a platinum-based catalyst is used simultaneously.

According to another embodiment of the present invention, the reduction reaction is carried out by a fixed bed hydrogenation or a fluidized bed hydrogenation.

According to another embodiment of the present invention, when a fixed bed catalytic hydrogenation is used, the pressure of the hydrogen is from 0.5 to 12 MPa and the reaction temperature is from 40 to 110° C.

According to another embodiment of the present invention, when a fluidized bed catalytic hydrogenation is used, the pressure of the hydrogen gas is from 0.5 to 15 MPa and the reaction temperature is from 40 to 110° C.

In another aspect, the present invention provides 1,5-pentanediamine prepared by the method according to any one of the embodiments mentioned above.

The present method for purifying 1,5-pentanediamine is of concise process and simple operation, is suitable for industrial production, and can improve the quality of 1,5-pentanediamine product remarkably.

DETAILED DESCRIPTION OF THE INVENTION

Typical examples illustrating the features and advantages of the present invention will be described in detail in the following description. It should be understood that the invention can have various changes in various embodiments without departing from the scope of the invention and the description herein is by way of illustration only and is not intended to limit the invention.

The fermentation broth or enzyme conversion solution containing 1,5-pentanediamine is subjected to extraction and distillation to obtain the 1,5-pentanediamine to be purified, which contains 2,3,4,5-tetrahydropyridine impurity. In order to eliminate the effect of the impurity on the subsequent polymerization producing nylon, in the present invention, the 1,5-pentanediamine to be purified containing above-mentioned impurity is subject to reduction treatment to convert 2,3,4,5-tetrahydropyridine therein to piperidine. By doing so, the content of 2,3,4,5-tetrahydropyridine impurity in the purified 1,5-pentanediamine is less than 0.05 wt %, or even less than 0.03 wt %, and 1,5-pentanediamine product with a high quality is obtained, which meets the stringent requirements for 1,5-pentanediamine monomer in the preparation of polymers such as nylon.

The present invention provides a method for purifying 1,5-pentanediamine comprising: providing 1,5-pentanediamine to be purified; and treating said 1,5-pentanediamine to be purified by use of reduction reaction to obtain purified 1,5-pentanediamine.

In the present invention, the 1,5-pentanediamine to be purified contains 2,3,4,5-tetrahydropyridine impurity.

In the present invention, after the reduction of 1,5-pentanediamine to be purified, 2,3,4,5-tetrahydropyridine is reduced to piperidine. The boiling point of piperidine is significantly different from that of 1,5-pentanediamine, which makes them to be easily separated in the subsequent distillation process, such that the content of piperidine in the purified 1,5-pentanediamine is controlled at a level of no more than 0.05 wt % relative to 1,5-pentanediamine, preferably no more than 0.03 wt %, the content is in weight percentage and is based on the weight percentage of 1,5-pentanediamine in the purified 1,5-pentanediamine. Due to the absence of unsaturated bond in piperidine, there is no significant effect on the subsequent polymerization of pentanediamine during the actual production, and thus the conversion of 2,3,4,5-tetrahydropyridine to piperidine is also of significance in practical production.

In the present invention, the 1,5-pentanediamine to be purified, which contains 2,3,4,5-tetrahydropyridine as impurity, may present in form of 1,5-pentanediamine containing 2,3,4,5-tetrahydropyridine impurity, or an organic solution or an aqueous solution thereof. In particular, the 1,5-pentanediamine to be purified can be obtained by basifying a solution containing 1,5-pentanediamine salt, followed by extraction or evaporation, and the content of 1,5-pentanediamine, except the solvent and water, is more than 99%.

In the present invention, there is not particular limit to the source of the 1,5-pentanediamine to be purified. The 1,5-pentanediamine to be purified can be prepared by chemical methods. Suyama et al. (*The method of decarboxylation of lysine*, fourth edition, Yakugaku Zasshi (1965), Vol. 85(6), pp, 531-533) discloses a process in which the lysine is boiled in cyclohexane containing tetrahydronaphthalene peroxides to produce pentanediamine. Japanese Unexamined Patent Publication (Kokai) No. SHO-60-23328 discloses a method for producing pentanediamine from lysine using vinyl ketone compounds of 2-cyclic vinyl ester as a catalyst. Pentanediamine can also be prepared by biological methods. For example, an enzymatic conversion solution is obtained by the action of pentanediamine decarboxylase on lysine, and thereby extracting pentanediamine (See JP 200400114A). The resulting lysine can be simultaneously converted to pentanediamine during the fermentation by up-regulating the expression of lysine decarboxylase in a lysine-producing strain, for example by gene technology, or by recombinant expression of lysine decarboxylase, and thus pentanediamine fermentation broth is obtained by direct fermentation (See Construction of Recombinant *Corynebacterium glutamicum* Producing 1,5-Pentanediamine by One Step Method, Niu Tao, et al., CHINA BIOTECHNOLOGY, 2010, 30 (8): 93-99).

In the present invention, there is not particular limit to the method for producing the 1,5-pentanediamine to be purified, and any conventional method can be used. A solvent method, for example, can be used, which comprises the following steps: adding a base to the solution of the pentanediamine salt to adjust the pH value thereof; using a solvent to extract the pentanediamine therefrom; and separating the pentanediamine from the solvent (see JP 200400114A, JP2004222569A, CN101981202A). A precipitation method, for example, can be used, which comprises the following steps: mixing a solution of pentanediamine with a base to form pentanediamine phase and aqueous phase, and separating the pentanediamine from the pentanediamine phase (See JP2009096796A, JP2009131239A). A membrane filtration method, for example, can be used, which comprises the following steps: adding a base into a solution of the pentanediamine salt to adjust the pH value thereof; using a nano-membrane to filtrate the salt out; and obtain the aqueous solution of pentylenediamine accordingly (see CN101970393A). Also, a reaction process, for example, can be used, which comprises the following steps: subjecting the pentanediamine into a reaction to give a more readily separated compound; separating the compound therefrom; and reducing the resulting compound into pentanediamine (see CN102712569A, CN102056889A). In addition, CN101356151A discloses the addition of sufficient amount of ammonia or hydrazine into the pentanediamine salt to form a liquid phase of pentanediamine and ammonia/hydrazine and a solid phase of an inorganic salt, followed by separation and extraction of pentanediamine.

In the present invention, the method for extracting or preparing the pentanediamine to be purified is not particularly limited. For example, the method disclosed in PCT/CN2013/071044, PCT/CN2013/071045, JP2009096796A, JP 2009131239 A and the like, can be used.

The organic solvent used to dissolve and extract 1,5-pentanediamine in the present invention refers to the one which does not react with 1,5-pentanediamine, maintains inert during the chemical hydrogenation reduction and has a certain solubility to 1,5-pentanediamine. Conventional chemical solvents may be alcoholic solvent such as ethanol and butanol.

In the present invention, there is no limit the way for carrying out the reduction reaction. A reduction reaction can be carried out by using a chemical reducing agent or by electrochemical reduction. The reducing agents include, but not limited to, active metal elements such as Na, Al, Zn, Fe and the like, metal hydrides such as lithium aluminum hydride ($LiAlH_4$), sodium borohydride ($NaBH_4$), zinc borohydride ($Zn(BH_4)_2$), potassium borohydride ($KBH_4$) and the like, reductive non-metallic substances such as $H_2$, C, Si, etc., alkali metal elements such as Li, Na, K and the like, reductive oxides such as CO, $SO_2$, $H_2O_2$ and the like, non-metallic hydrides such as $H_2S$, $NH_3$, HCl, $CH_4$, and the like, reductive salts such as $Na_2SO_3$, $FeSO_4$ and the like, and other reductive substances such as stannous chloride ($SnCl_2$), oxalic acid ($H_2C_2O_4$), ethanol ($C_2H_5OH$) and the like.

In one embodiment of the present invention, the reducing agent is hydrogen gas. In particular, the 1,5-pentanediamine to be purified and hydrogen gas can be passed through a fixed bed packed with a catalyst; 1,5-pentanediamine to be purified and hydrogen gas can also be reacted in a fluidized bed reactor having the catalyst. In another embodiment of the present invention, the reducing agent is a metal hydride, and the 1,5-pentanediamine to be purified and the metal hydride are mixed and heated to remove 2,3,4,5-tetrahydropyridine, wherein the metal hydride includes, but is not limited to, $NaBH_4$, $KBH_4$, $LiAlH_4$, the amount of substance of which is about from 1 to 2 times of that of 2,3,4,5-tetrahydropyridine in the 1,5-pentanediamine to be purified.

In the present invention, the reduction reaction conditions of the metal hydride are as follows: the amount of the metal hydride to be added depends on the content of 2,3,4,5-tetrahydropyridine in 1,5-pentanediamine, and is about from 1 to 2 times of 2,3,4,5-tetrahydropyridine in the 1,5-pentanediamine to be purified in the amount of substance. The reaction temperature is between about 0° C. and 90° C., preferably about 20° C. and 60° C. If the temperature is too high, although the reaction is accelerated, some side-reactions may take place, which would increase the impurities in the pentanediamine. The reaction time is about from 0.5 to 1 hour.

In the present invention, a protic solvent such as water, alcohol and the like may be added in an amount of 1% to 15% by weight of the metal hydride as a co-solvent for the metal reducing agent.

In the present invention, after the reduction reaction, distillation can be continued to further remove the reaction product and purify 1,5-pentanediamine. The distillation step can be a combination of one or more operations in vacuum distillation, flashing, and distillation.

In the present invention, when the reducing agent is hydrogen gas, a fixed bed hydrogenation or a fluidized bed hydrogenation may be used. The catalyst may be a nickel-based catalyst, a platinum-based catalyst, or other catalyst suitable for catalytic hydrogenation. The catalyst of the present invention is preferably a nickel-based catalyst, and more preferably a supported nickel-based catalyst, wherein the carrier may be aluminum or alumina, or it may be a natural mineral such as diatomaceous earth, or an adsorbent such as activated carbon.

In the invention, the preferred process conditions for the purification by using the fixed bed catalytic hydrogenation are: hydrogen pressure of 0.5 to 10 MPa, and the reaction temperature of hydrogenation purification of 40 to 110° C.

In the present invention, the preferred process conditions for the purification by using the fluidized bed catalytic hydrogenation are: hydrogen pressure of 0.5 to 15 MPa, the reaction temperature of hydrogenation purification of 40 to 110° C., the addition amount of the catalyst of 0.1 wt % to 5 wt % based on the weight of 1,5-pentanediamine in the 1,5-pentanediamine to be purified.

In the invention, 2,3,4,5-tetrahydropyridine impurity is converted into saturated piperidine by chemical reduction. The content of 2,3,4,5-tetrahydropyridine in 1,5-pentanediamine is reduced to less than 0.1% by weight, preferably less than 0.05% by weight, more preferably less than 0.03% by weight, or even less than 0.01% by weight. The damage of 2,3,4,5-tetrahydropyridine to polymerization producing nylon is eliminated. The piperidine produced by reduction reaction can be separated from 1,5-pentanediamine in subsequent distillation. The impact of piperidine without unsaturated bond on polymerization producing nylon is much lower than that of 2,3,4,5-tetrahydropyridine. There is nearly no 1,5-pentanediamine product lost, and not any more purity except 2,3,4,5-tetrahydropyridine would be produced in the process. The present invention can effectively remove impurities at a lower cost to obtain a purified 1,5-pentanediamine product with high quality.

After converting 2,3,4,5-tetrahydropyridine impurity into piperidine by the reduction method in the present invention, the resulting purified pentanediamine can further remove the converted piperidine, or is directly subjected to a subsequent process without removing piperidine. The method for removing piperidine includes, but is not limited to, use of ion exchange resins, activated carbon adsorption, extraction, or distillation extraction, etc. The above-mentioned method for removing piperidine may be used alone or in combination of two or more.

The metal reducing agent of the invention can directly supply a hydrogen source, and an imine can be conveniently reduced to amine without an additional catalyst. The reaction condition is mild, the process and operation is simple and the method is suitable for large-scale industrial production.

The invention will now be described in detail by way of specific examples to make the features and advantages of the invention clearer. But the invention is not limited to the examples given herein.

Among them, the 1,5-pentanediamine to be purified in the following examples can be obtained by extraction or distillation. Specifically, reference may be made to PCT/CN2013/071044, PCT/CN 2013/071045, JP 2009096796 A, JP 2009131239 A and the like.

The method for preparing the fermentation broth used in the examples can be found in Patent PCT/CN 2013/071044, PCT/CN2013/071045, JP 2009096796 A, JP 2009131239 A and the like.

In the examples and comparative examples listed herein, the following test methods were used:
1. Pentanediamine Gas Chromatography (GC)
   The test methods for pentanediamine and 2,3,4,5-tetrahydropyridine:
   See CN102782146 A, using gas phase normalization method.
2. Nylon color detection method:
   GB-T 2409-1980, using KONICA MINOLTA CM-3600A instrument.

Example 1

To a 500 mL round bottom flask equipped with a stirrer and a thermometer was charged 250 g of 1,5-pentanediamine to be purified in a mass concentration of 99%. The 1,5-pentanediamine to be purified contained 500 mg organic impurity 2,3,4,5-tetrahydropyridine (THP) (6 mmol, 0.2 wt %, based on the weight of 1,5-pentanediamine in the 1,5-pentanediamine to be purified). Then, 240 mg $NaBH_4$ (6 mmol) was added to the round bottom flask. The temperature of the solution in the flask was controlled at 5 to 10° C. After stirring for 1 hour, a small amount of water was added to quench the reaction.

1,5-pentanediamine in the solution after chemical reduction reaction was sampled and analyzed. The analytical results showed that 1,5-pentanediamine had a purity of 99.41%, the content of THP was 0.06 wt % and the content of piperidine was 0.16 wt % (normalized).

The above-mentioned reduced 1,5-pentanediamine solution was subjected to distillation, and 1,5-pentanediamine was further separated from piperidine impurity to obtain the purified 1,5-pentanediamine.

The purified 1,5-pentanediamine was detected by GC. The results showed that 1,5-pentanediamine had a purity of 99.86 wt %, the content of THP was 0.06 wt % and the content of piperidine was 0.05 wt % (normalized).

Example 2

To a 500 mL round bottom flask equipped with a stirrer and a thermometer was charged 250 g of 1,5-pentanediamine to be purified in a mass concentration of 99%. The 1,5-pentanediamine to be purified contained 500 mg organic impurity THP (6 mmol, 0.2%). 25 mL of methanol and 240 mg of $NaBH_4$ (6 mmol) were added to the round bottom flask, and the temperature of the solution in the flask was controlled at 0 to 10° C. After stirring for 1 hour, a small amount of water was added to quench the reaction.

1,5-pentanediamine in the solution after chemical reduction reaction was sampled and analyzed. The analytical results showed that 1,5-pentanediamine had a purity of 99.46%, the content of THP was 0.05%, the content of piperidine was 0.15% (normalized).

The above-mentioned reduced 1,5-pentanediamine solution was subjected to distillation, and 1,5-pentanediamine was further separated from the piperidine impurity to obtain purified 1,5-pentanediamine.

The purified 1,5-pentanediamine was detected by GC. The results showed that 1,5-pentanediamine had a purity of 99.89%, the content of THP was 0.05% and the content of piperidine was 0.02% (normalized).

Example 3

To a 500 mL round bottom flask equipped with a stirrer and a thermometer was charged 250 g of 1,5-pentanediamine to be purified in a mass concentration of 99%. The 1,5-pentanediamine to be purified contained 500 mg organic impurity THP (6 mmol, 0.2%). 30 mL of purified water and 240 mg of $NaBH_4$ (6 mmol) were added to the round bottom flask, and the reaction temperature was controlled at 10 to 15° C. After stirring for 0.5 hour, a small amount of water was added to quench the reaction.

1,5-pentanediamine in the solution after chemical reduction reaction was sampled and analyzed. The results showed that 1,5-pentanediamine had a purity of 99.32%, the content of THP was 0.04% and the content of piperidine was 0.15% (normalized).

The above-mentioned reduced 1,5-pentanediamine solution was subjected to distillation, and 1,5-pentanediamine was further separated from the piperidine impurity to obtain purified 1,5-pentanediamine.

The purified 1,5-pentanediamine was detected by GC. The results showed that 1,5-pentanediamine had a purity of 99.91%, the content of THP was 0.04% and the content of piperidine was 0.01% (normalized).

Example 4

To a 500 mL round bottom flask equipped with a stirrer and a thermometer was charged 250 g of 1,5-pentanediamine to be purified in a mass concentration of 99%. The 1,5-pentanediamine to be purified contained 500 mg organic impurity THP (6 mmol, 0.2%). 480 mg of $NaBH_4$ (12 mmol) was added to the round bottom flask. After stirring at 15 to 20° C. for 0.5 hour, a small amount of water was added to quench the reaction.

1,5-pentanediamine in the solution after chemical reduction reaction was sampled and analyzed. The analytical results showed that 1,5-pentanediamine had a purity of 99.36%, the content of THP was 0.05% and a content of piperidine was 0.14% (normalized).

The above-mentioned reduced 1,5-pentanediamine solution was subjected to distillation, and 1,5-pentanediamine was further separated from the piperidine impurity to obtain purified 1,5-pentanediamine.

The purified 1,5-pentanediamine was detected by GC. The results showed that 1,5-pentanediamine had a purity of 99.90%, the content of THP was 0.05% and the content of piperidine was 0.01% (normalized).

Example 5

To a 500 mL round bottom flask equipped with a stirrer and a thermometer was charged 250 g of 1,5-pentanediamine to be purified in a mass concentration of 99%. The 1,5-pentanediamine to be purified contained 500 mg organic impurity THP (6 mmol, 0.2%). 228 mg of $LiAlH_4$ (6 mmol) was added to the round bottom flask and a reduction reaction was conducted at 20 to 25° C. for 1 hour with stirring. A small amount of water was added to quench the reaction.

1,5-pentanediamine in the solution after chemical reduction reaction was sampled and analyzed. The results showed that 1,5-pentanediamine had a purity of 99.45%, the content of THP was 0.03%, the content of piperidine was 0.16% (normalized).

The above-mentioned reduced 1,5-pentanediamine solution was subjected to distillation, and 1,5-pentanediamine was further separated from the impurity piperidine to obtain purified 1,5-pentanediamine.

The purified 1,5-pentanediamine was detected by GC. The results showed that 1,5-pentanediamine had a purity of 99.87%, the content of THP was 0.03% and the content of piperidine was 0.03% (normalized).

Example 6

A solution of pentanediamine in butanol (the content of pentanediamine was 6 wt %) prepared according to the extraction process of the Chinese patent application publication CN101981202A was passed through a distillation apparatus to fractionate out butanol, so as to obtain 1,5-pentanediamine to be purified. The content of 1,5-pentanediamine was 98% and the content of THP was 0.21%.

A 100 mL nickel-based supported catalyst (CRI International Ltd., KL6565) was charged in the middle of a stainless steel reactor having an inner diameter of 20 mm and a length of 720 mm. Quartz sands with a particle size of 20 to 40 mesh were added as a support layer in the lower part of the reactor, and a small amount of 20 to 40 mesh quartz sands were added in the upper part of the reactor to adjust the liquid distribution. The temperature was automatically controlled by using electric heating. After the catalyst was activated, the 1,5-pentanediamine to be purified was mixed with hydrogen gas and passed through the catalyst bed from top to bottom. A catalytic hydrogenation reaction was carried out under the following conditions: the pressure of hydrogen gas in reactor was controlled at 3 MPa (gauge pressure); the reaction temperature was kept in a range of from 50 to 80° C.; and the feed flow rate of 1,5-pentanediamine to be purified was of 200 mL/hour. Thus, 2,3,4,5-tetrahydropyridine in the 1,5-pentanediamine to be purified was converted to piperidine.

After reacting in above reactor, the reaction product flowing out from the outlet of the reactor was cooled, liquefied, and quantified by gas chromatography.

1,5-pentanediamine in the solution after catalytic hydrogenation reaction was sampled and analyzed. The results showed that 1,5-pentanediamine had a purity of 99.51%, the content of 2,3,4,5-tetrahydropyridine was 0.006%, and the content of piperidine was 0.23% (normalized).

Example 7

A solution of pentanediamine in butanol (the content of pentanediamine was 6 wt %) prepared according to the extraction process of the Chinese patent application publication CN101981202A was passed through a distillation apparatus to fractionate out butanol, so as to obtain 1,5-pentanediamine to be purified. The content of 1,5-pentanediamine was 98% and the content of THP was 0.21%.

A 100 mL nickel-based supported catalyst (CRI International Ltd., KL7767) was charged in the middle of a stainless steel reactor having an inner diameter of 20 mm and a length of 720 mm. Quartz sands with a particle size of 20 to 40 mesh were added as a support layer in the lower part of the reactor, and a small amount of 20 to 40 mesh quartz sands were added in the upper part of the reactor to adjust the liquid distribution. The temperature was automatically controlled by using electric heating. After the catalyst was activated, the 1,5-pentanediamine to be purified was mixed with hydrogen gas and passed through the catalyst bed from top to bottom. A catalytic hydrogenation reaction was carried out under the following conditions: the pressure of hydrogen gas in reactor was controlled at 0.5 MPa (gauge pressure); the reaction temperature was kept in a range of 100 to 110° C.; and the feed flow rate of 1,5-pentanediamine to be purified was of 50 mL/hour. Thus, 2,3,4,5-tetrahydropyridine in the 1,5-pentanediamine to be purified was converted to piperidine.

After reacting in above reactor, the reaction product flowing out from the outlet of the reactor was cooled, liquefied, and quantified by gas chromatography.

1,5-pentanediamine in the solution after catalytic hydrogenation reaction was sampled and analyzed. The results showed that 1,5-pentanediamine had a purity of 99.52%, the content of 2,3,4,5-tetrahydropyridine was 0.003%, and the content of piperidine was 0.20% (normalized).

Example 8

A solution of pentanediamine in butanol (the content of pentanediamine was 6 wt %) prepared according to the extraction process of the Chinese patent application publication CN101981202A was passed through a distillation apparatus to fractionate out butanol, so as to obtain 1,5-pentanediamine to be purified. The content of 1,5-pentanediamine was 98% and the content of THP was 0.21%.

A 100 mL nickel-based supported catalyst (CRI International Ltd., KL7767) was charged in the middle of a stainless steel reactor having an inner diameter of 20 mm and a length of 720 mm. Quartz sands with a particle size of 20 to 40 mesh were added as a support layer in the lower part of the reactor, and a small amount of 20 to 40 mesh quartz sands were added in the upper part of the reactor to adjust the liquid distribution. The temperature was automatically controlled by using electric heating. After the catalyst was activated, the 1,5-pentanediamine to be purified was mixed with hydrogen gas and passed through the catalyst bed from top to bottom. A catalytic hydrogenation reaction was carried out under the following conditions: the pressure of hydrogen gas in reactor is controlled at 10 MPa (gauge pressure); the reaction temperature is kept in a range of 40 to 60° C.; and the feed flow rate of 1,5-pentanediamine to be purified is of 600 mL/hour. Thus, 2,3,4,5-tetrahydropyridine in the 1,5-pentanediamine to be purified was converted to piperidine.

After reacting in above reactor, the reaction product flowing out from the outlet of the reactor was cooled, liquefied, and quantified by gas chromatography.

1,5-pentanediamine in the solution after catalytic hydrogenation reaction was sampled and analyzed. The results showed that 1,5-pentanediamine had a purity of 99.47%, the content of 2,3,4,5-tetrahydropyridine was 0.004%, and the content of piperidine was 0.20% (normalized).

Example 9

A solution of pentanediamine in butanol (the content of pentanediamine was 6 wt %) prepared according to the extraction process of the Chinese patent application publication CN101981202A was passed through a distillation apparatus to fractionate out butanol, so as to obtain 1,5-pentanediamine to be purified. The content of 1,5-pentanediamine was 98% and the content of 2,3,4,5-tetrahydropyridine was 0.21%.

To a 5 L autoclave, 2 L of above-mentioned pentanediamine liquid was added, and then 1.6 g of activated skeleton nickel catalyst (made by Jinzhou catalyst plant). The reaction was carried out for a total of 6 hours under the hydrogen pressure in the autoclave being controlled at 12 MPa (gauge pressure), with the reaction temperature of 105 to 110° C. and stirring. Then the catalyst was separated by precipitation to give a solution of the pentanediamine. The resulting product was quantified by gas chromatography.

1,5-pentanediamine in the solution after catalytic hydrogenation reaction was sampled and analyzed. The results showed that 1,5-pentanediamine had a purity of 99.51%, the content of 2,3,4,5-tetrahydropyridine was 0.01%, and the content of piperidine was 0.18% (normalized).

Example 10

A solution of pentanediamine in butanol (the content of pentanediamine was 6 wt %) prepared according to the extraction process of the Chinese patent application publication CN101981202A was passed through a distillation apparatus to fractionate out butanol, so as to obtain 1,5-pentanediamine to be purified. The content of 1,5-pentanediamine was 98% and the content of THP was 0.21%.

To a 5 L autoclave, 2 L of above-mentioned pentanediamine liquid was added, and then 90 g of activated skeleton nickel catalyst (made by Jinzhou catalyst plant) and 10 g of activated palladium-based supported catalyst (CRI International Ltd. KL7767) were added. The reaction was carried out for a total of 2 hours under the hydrogen pressure in the autoclave being controlled at 12 MPa (gauge pressure), with the reaction temperature of 45° C. and stirring. Then the catalyst was separated by precipitation to give a solution of the pentanediamine. The resulting product was quantified by gas chromatography. 1,5-pentanediamine in the solution after catalytic hydrogenation reaction was sampled and analyzed. The results showed that 1,5-pentanediamine had a purity of 99.51%, the content of 2,3,4,5-tetrahydropyridine was 0.007%, and the content of piperidine was 0.19% (normalized).

Comparative Example 1

To a 500 mL round bottom flask equipped with a stirrer and a thermometer was charged 250 g of 1,5-pentanediamine in a mass concentration of 99% containing 500 mg of organic impurity THP (6 mmol, 0.2%).

Application Example

In a 100 L of enamel kettle, the air was replaced with nitrogen by means of a vacuum purge gas and the enamel kettle was protected with nitrogen. A 40 kg aqueous solution of 1,5-pentanediamine was added to the kettle and the solution was heated to 60° C. with stirring. To the solution, adipic acid (made by PetroChina Liaoyang Petrochemical, the same below) was added to adjust pH of solution to 7.5, to prepare a solution of pentanediamine adipic acid nylon salt.

In a 100 L polymerization kettle, the air was replaced with nitrogen and the nylon salt solution was transferred to the polymerization kettle. The temperature of the oil bath rose to 230° C. When the pressure in the kettle rose to 1.73 MPa, a gas release will occur. When the temperature in the kettle reached 265° C., the kettle was vacuumized to −0.06 MPa (vacuum gauge pressure), and this vacuum was maintained for 20 min, to make the corresponding nylon.

The polymerization kettle was filled with nitrogen gas until the pressure thereof reached 0.5 MPa, and then the contents of the kettle in a melt state began to be discharged, and pelletized using a pelletizer. After drying under vacuum for 8 hours at 80° C., the color detection was carried out.

The polyamide was prepared from the 1,5-pentanediamine obtained in Examples 1 to 10 and Comparative Example 1 according to above method, and the yellow index of the obtained polyamide was examined. The results are shown in Table 1.

TABLE 1

| | The Content of THP in the Purified 1,5-Pentanediamine | Yellow Index of Nylon |
|---|---|---|
| Example 1 | 0.06% | 6 |
| Example 2 | 0.05% | 5 |
| Example 3 | 0.04% | 5 |
| Example 4 | 0.05% | 6 |
| Example 5 | 0.03% | 4 |
| Example 6 | 0.006% | 2 |
| Example 7 | 0.003% | 1 |
| Example 8 | 0.004% | 1 |
| Example 9 | 0.01% | 3 |
| Example 10 | 0.007% | 2 |
| Comparative Example 1 | 0.2% | 15 |

Table 1 lists the content of THP in the 1,5-pentanediamine prepared in the examples and comparative example of the present invention, and the yellow index of nylon prepared from above 1,5-pentanediamine as a starting material. The data in table 1 shows that the content of THP in 1,5-pentanediamine can be controlled within 0.06% and the yellow index of nylon is no more than 6 according to the purification method of the present invention. When the hydrogen gas is used as the catalyst for the reduction reaction, the content of THP can even be controlled within 0.007%, such that the yellow index of the nylon is about 1. Compared with the comparative example, the yellow index is greatly reduced and the quality is improved significantly.

Unless otherwise specified, the terms used in the present invention have the meanings as commonly understood by one skilled in the art.

The embodiments described herein are for illustrative purposes only and are not intended to limit the scope of the invention. Various alternatives, alterations and modifications can be made by one skilled in the art within the scope of the invention. The present invention is not limited to the above-described embodiments, but only defined by the claims.

The invention claimed is:

1. A method for purifying 1,5-pentanediamine, comprising:
   providing a mixture containing 1,5-pentanediamine to be purified and 2,3,4,5-tetrahydropyridine; and
   treating said mixture by use of a reduction reaction to reduce said 2,3,4,5-tetrahydropyridine to piperidine thereby obtaining a first purified 1,5-pentanediamine composition,
   wherein the reduction reaction comprises an electrochemical reduction or a reduction with use of a reducing agent,
   wherein the reducing agent comprises hydrogen gas, (i) the pressure of the hydrogen gas is 0.5 MPa, and the temperature of the reduction reaction is from 100 to 110° C., or (ii) the pressure of the hydrogen gas is 10 MPa, the temperature of the reduction reaction is from 40 to 60° C., and the reduction reaction process comprises:
   charging the nickel-based supported catalyst in a stainless steel reactor having an inner diameter of 20 mm and a length of 720 mm, wherein the reactor comprises quartz sands with a particle size of 20 to 40 mesh as a support layer in the lower part of the reactor and a small amount of 20 to 40 mesh quartz sands in the upper part of the reactor to adjust the liquid distribution; and
   after the catalyst was activated, mixing the 1,5-pentanediamine to be purified with the hydrogen gas and passing resultant mixture through the catalyst bed from top to bottom.

2. The method according to claim 1, wherein the content of 2,3,4,5-tetrahydropyridine impurity in the first purified 1,5-pentanediamine composition is less than 0.05 wt %.

3. The method according to claim 1, wherein the content of 2,3,4,5-tetrahydropyridine impurity in the first purified 1,5-pentanediamine composition is less than 0.03 wt %.

4. The method according to claim 1, further comprising a distillation step to remove the piperidine from the first purified 1,5-pentanediamine composition to obtain a second purified 1,5-pentanediamine composition, so that the content of piperidine in the second purified 1,5-pentanediamine composition is less than 0.05 wt %, based on the weight of 1,5-pentanediamine in the mixture.

5. The method according to claim 4, wherein the content of piperidine in the second purified 1,5-pentanediamine composition is less than 0.03 wt %.

\* \* \* \* \*